United States Patent [19]

Bailey et al.

[11] Patent Number: 5,541,114

[45] Date of Patent: Jul. 30, 1996

[54] SEQUENCING OF PROTEIN IMMOBILIZED ON POLYTETRAFLUOROETHYLENE SUPPORTS

[75] Inventors: Jerome M. Bailey, Duarte; John E. Shively, Arcadia, both of Calif.

[73] Assignee: City of Hope, Duarte, Calif.

[21] Appl. No.: 204,416

[22] PCT Filed: Jul. 23, 1992

[86] PCT No.: PCT/US92/06083

§ 371 Date: Mar. 15, 1994

§ 102(e) Date: Mar. 15, 1994

[87] PCT Pub. No.: WO94/02855

PCT Pub. Date: Feb. 3, 1994

[51] Int. Cl.$^6$ .................................................. G01N 33/68
[52] U.S. Cl. ............................ 436/89; 530/334; 530/335; 530/337; 530/344; 530/402; 530/412; 530/417
[58] Field of Search ..................... 436/86, 89; 530/334, 530/335, 337, 344, 402, 412, 417

[56] References Cited

U.S. PATENT DOCUMENTS 3,843,443  10/1974  Fishman .......................... 195/63
5,061,635  10/1991  Shively ........................... 436/89

FOREIGN PATENT DOCUMENTS 0410323  7/1990  European Pat. Off. .

OTHER PUBLICATIONS

Pappin, et al., Analytical Biochemistry 187:10–19 (1990).

*Primary Examiner*—David A. Redding
*Attorney, Agent, or Firm*—Rothwell, Figg, Ernst & Kurz

[57] ABSTRACT

A method for sequencing proteins on a polytetrafluoroethylene support is described. The support is preferably porous. The sample to be sequenced may be transferred directly, e.g., by blotting, to the support. Covalent binding of the sample to the support is not required.

5 Claims, 3 Drawing Sheets

P - PRESSURE VALVE
BO - BLOW OUT VALVE
SW - SWITCHING VALVE
CFR - CONTINUOUS FLOW REACTOR
CF - CONVERSION FLASK
Q - QUAD VALVE

TUBING I.D.
—··—··— 0.2 mm
------ 0.3 mm
——— 0.5 mm
- - - - - 0.8 mm
▬▬▬ 1.0 mm

REAGENT, SOLVENT, OR WASTE BOTTLE

SEQUENCING OF PROTEIN IMMOBILIZED ON POLYTETRAFLUOROETHYLENE SUPPORTS

This invention was made with government support under Grant No. GM 46022 awarded by the National Institutes of Health. The government has certain rights in the invention.

FIELD OF THE INVENTION

This invention relates to the sequencing of peptides immobilized on preferably porous polytetrafluoroethylene supports. More particularly, the invention relates to automated C-terminal and N-terminal sequencing of peptides blotted from a gel onto a porous polytetrafluoroethylene support.

BACKGROUND OF THE INVENTION

Various methods for the N-terminal and C-terminal sequencing of peptides are known. Application of this chemistry to peptides covalently attached to a solid support has facilitated automation. Perceived advantages of covalently immobilizing a peptide or protein to a solid support include: elimination of sample washout thereby resulting in high initial and repetitive yields, the ability to use reagents and solvents optimal for derivatization and washing, and the ability efficiently to wash the sample to remove reaction by-products resulting from thiohydantoin formation, thereby creating a potential for a low chemical background.

The concept of solid phase sequencing for N-terminal Edman chemistry was proposed by Laursen, *Eur. J. Biochem.* 20:89–102 (1971) and has since been used successfully by a number of groups for the Edman degradation (Laursen, et al., *FEBS Lett.* 21:67–70 (1972); L'Italien, et al., *Anal. Biochem.* 127:198:212 (1982); L'Italien, *Methods in Protein Microcharacterization* (Shively, J. E., Ed.), pp. 279–314, Humana Press, Inc. (1986)).

Several different types of functional supports for the covalent immobilization of polypeptide samples for N-terminal sequencing have been described. These include polystyrene resins, polyacrylamide resins, and glass beads substituted with aminoalkyl or aminophenyl groups. See Laursen, et al., *Methods Biochem. Anal.* 26:201–284 (1980).

Initial attempts at C-terminal sequencing from covalently attached peptides using thiocyanate chemistry were made by several groups. Williams, et al. *FEBS Lett.* 54: 353–357 (1975) were able to perform 1–3 cycles on peptides (1 micromol) covalently attached to N-hydroxysuccinimide activated glass beads using 12N HCl for cleavage of the peptidylthiohydantoins. Utilizing this same procedure, Rangarajan, et al., *Biochem. J.* 157:307-316 (1976) were able to perform six cycles on ribonuclease (1 μmol) covalently coupled to glass beads with a cycle time of 5 to 6 hours. Three successful cycles, with HPLC identification of the released amino acid thiohydantoins, were performed by Meuth, et al., *Biochem.* 21:3750–3757 (1982) on a 22-amino acid polypeptide (350 nmol) covalently linked to a carbonyldiimidazole activated aminopropyl glass. These authors used thiocyanic acid for derivatization to a peptidylthiohydantoin and acetohydroxamate for cleavage, further reducing the time per cycle to 3 hours. A more recent report by Inglis, et al., *Methods in Protein Sequence Analysis* (Wittman-Lebold, B., Ed.) pp. 137–144, Springer-Verlag (1989) reports the sequential degradation of nine residues from a synthetic decapeptide (30 nmol) covalently coupled to glass beads with a cycle time of 48 min. However, no experimental details were given. More recent studies have involved the use of carboxylic acid modified PVDF (Bailey, et al., *Carboxy terminal sequencing: Automation and application to the solid phase. In Techniques in Protein Chemistry: II* (Villafranca, J. J.,Ed.) pp. 115–129 (Academic Press, Inc.) (1991)), carboxylic acid modified polyethylene (Shenoy, et al. *Protein Science* 1:58–67 (1992), and a disuccinamidoyl carbonate polyamide resin (Hawke, et al., *Met. Protein Sequence Analysis* (Jornvall/Hoog/Gustavsson Eds.) pp. 35–45, Birkhauser-Verlag, Basel (1991).

Currently PVDF is a preferred support for N-terminal sequencing, and for blotting of purified proteins from gels, such as SDS gels. However, in C-terminal sequencing procedures PVDF turns black and dissolves, frequently limiting some C-terminal sequencing procedures to a single cycle.

In addition to these problems presented by prior art supports, the need for covalent attachment inherently results in sample loss. For that reason, proteins are now blotted onto PVDF for N-terminal sequencing. However, for C-terminal sequencing the protein samples must be eluted from PVDF and applied to a different support.

SUMMARY OF THE INVENTION

Pursuant to one aspect of this invention, a polytetrafluoroethylene support, preferably porous, is provided for blotting of proteins from gels and for both N-terminal and C-terminal sequencing. The supports provided by this invention are chemically inert and, hence, do not degrade under the conditions of N-terminal or C-terminal sequencing. Proteins are strongly adherent to polytetrafluoroethylene supports and are not washed off by solvents typically used in sequencing, such as methanol, dimethylformamide, ethyl acetate and acetonitrile. Covalent coupling is not required.

DESCRIPTION OF THE TERMINAL SEQUENCER OF FIG. 1

Figure 1:
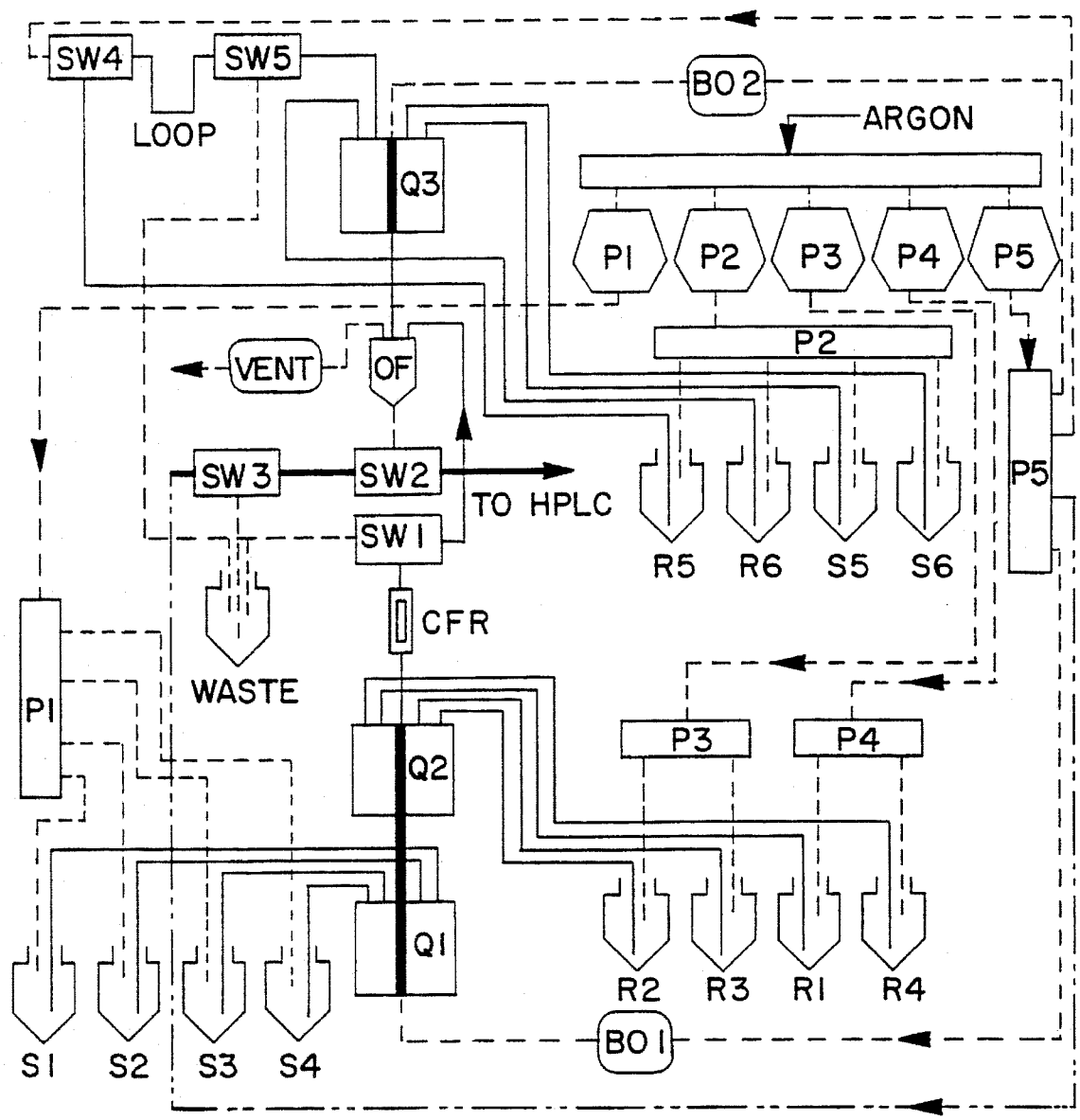
FIG. 1 is a schematic depiction of a C-terminal sequencer useful in the practice of the invention.
Figure 1:
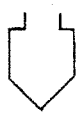
Figure 2A:
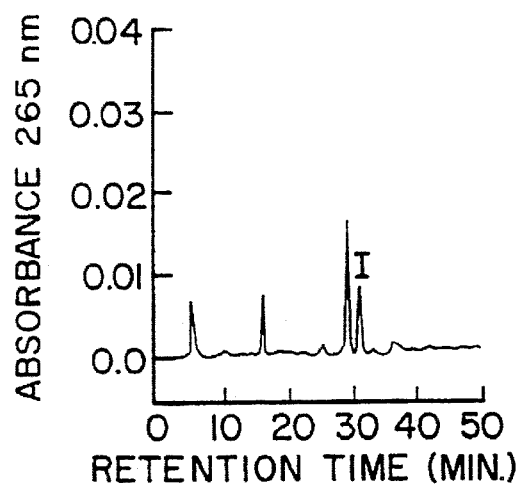
FIG. 2 depicts chromatograms which indicate the result in each of four cycles of C-terminal sequencing in the sequencer of FIG. 1 of β-lactoglobulin (350 pmol) noncovalently applied to a polytetrafluoroethylene support.
Figure 2B:
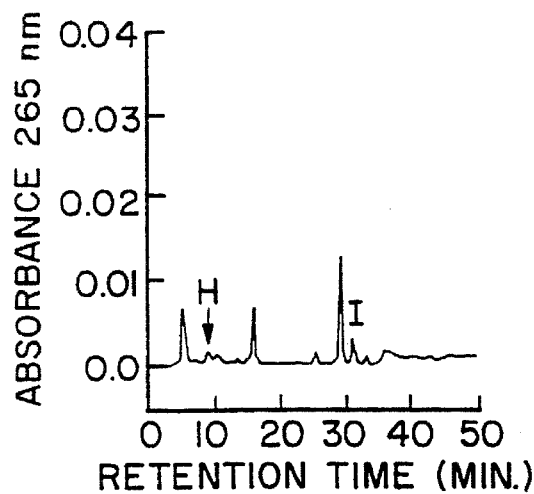
Figure 2C:
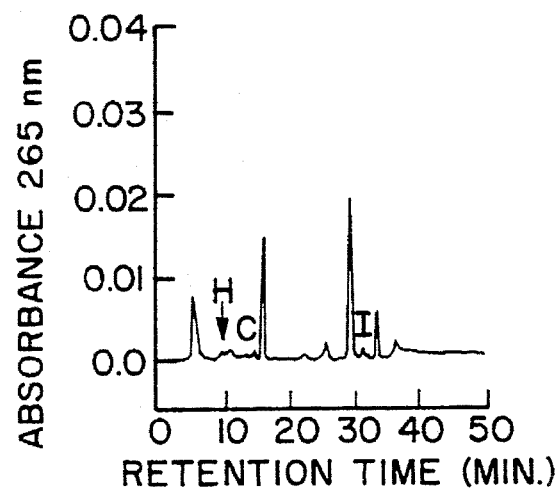
Figure 2D:
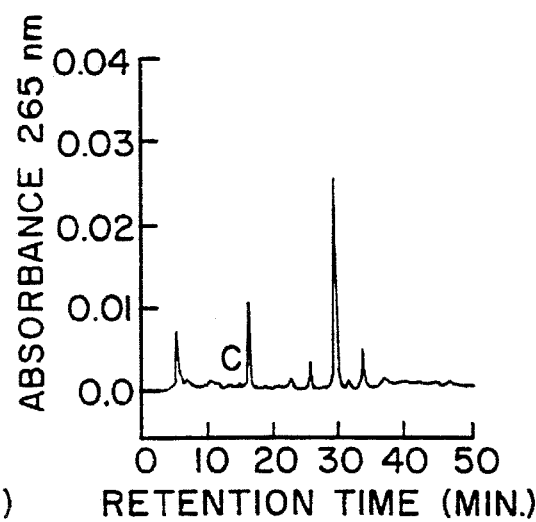
Figure 3A:
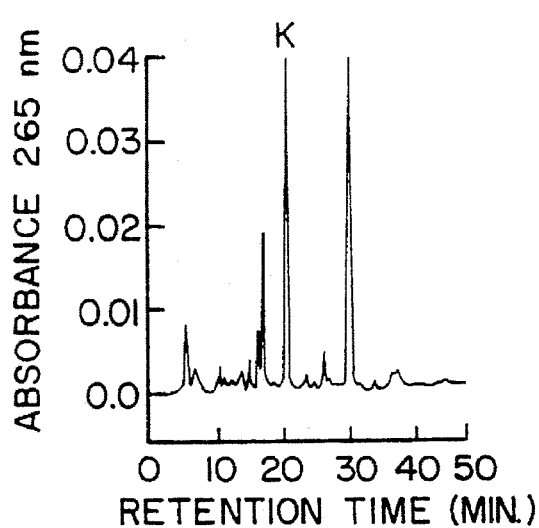
FIG. 3 depicts chromatograms which indicate the result in each of four cycles of C-terminal sequencing in the sequencer of FIG. 1 of superoxide dismutase (5.2 nmol) noncovalently applied to a polytetrafluoroethylene support.
Figure 3B:
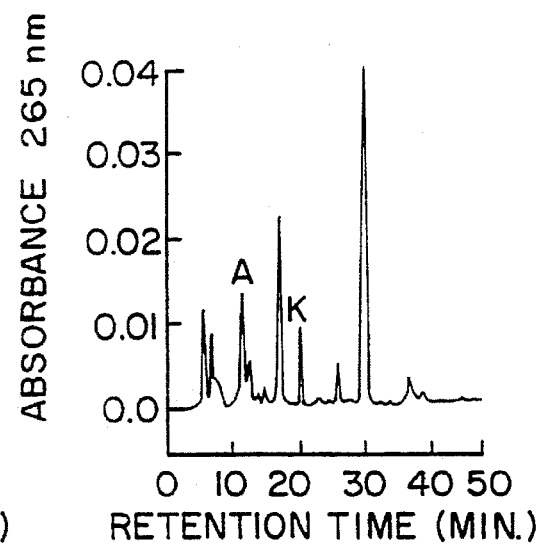
Figure 3C:
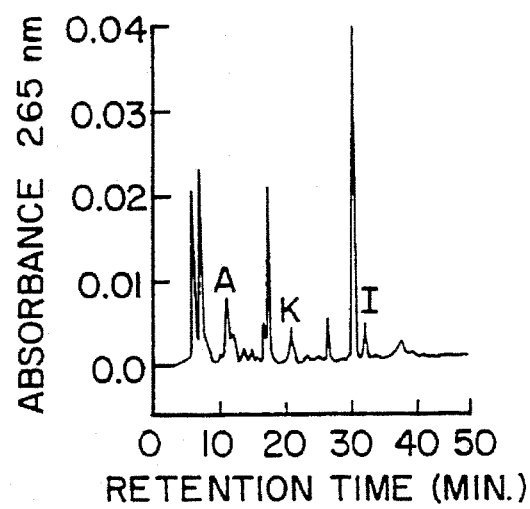
Figure 3D:
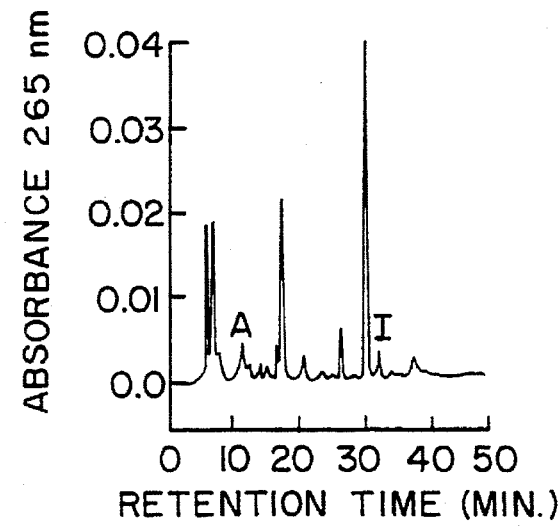

The overall design of the sequencer shown by FIG. 1 is similar in some respects to the gas phase N-terminal sequencer described by Calaycay, et al., *Anal. Biochem.* 192:23–31 (1991).

The reagent and solvent bottles associated with the instrument depicted by FIG. 1 are shown. Five reagent bottles, R1–R5, and five solvent bottles, S1–S5, are utilized in the practice of the invention as illustrated by the ensuing examples. Reagents from bottles R1–R4 and solvents from bottles S1–S4 are delivered to the continuous flow reactor (CFR). Reagent from bottle R5 and solvent from bottle S5 are delivered to the conversion flask (CF). In N-terminal sequencing, the CF serves to convert the ATZ derivative of the cleaved amino acid into a PTH (phenylthiohydantoin) just before analysis by HPLC. In C-terminal sequencing, the CF serves as a place to hold the cleaved thiohydantoin amino acid just prior to injection into the HPLC.

The composition of the reagents and solvents is set forth in Table 1.

TABLE 1

Composition of Reagents and Solvents

| | |
|---|---|
| R1 | 10% Triethylamine in methanol |
| R2 | Diphenyl phosphoroisothiocyanatidate in acetonitrile (3.0M) |
| R3 | 0.10M sodium trimethylsilanolate in 50% methanol, 50% t-butyl alcohol |
| R4 | pyridine |
| R5 | 2.0% trifluoroacetic acid in water |
| R6 | — |
| S1 | Heptane |
| S2 | Methanol |
| S3 | Dimethylformamide |
| S4 | Heptane |
| S5 | Methanol |
| S6 | — |

To deliver the various reagents and solvents to the CFR a gentle pressure (1.5 atms) of argon is applied to each bottle. Argon was chosen because of its chemical inertness. Other suitable inert gases could be helium and nitrogen. There are a total of 5 pressure regulators (P1–P5). P1 is for S1–S4, P2 is for S5, S6, R5, and R6, P3 is for R2 and R3, P4 is for R1 and R4, and P5 is for blow out functions and argon delivery functions (drying, etc.). When it is time to deliver a reagent (for example, R1), a solenoid actuated valve on P4 is opened in order to let the argon pass through the valve to the bottle (R1). Since each bottle is sealed, the argon pressure pushes the solvent through the line at the bottom of each bottle to the valve block (in this case Q2). There a solenoid actuated valve on Q2 and a valve on SW1 (for venting) is opened to allow the solvent to flow into the valve block, Q2 and on into the CFR. Once the CFR is full, the flow is stopped by closing the valves and the reaction is allowed to continue for the desired length of time. After the reaction the Angar valve (BO 1) and SW1 (to waste) is opened to allow argon to pass through the valve blocks Q1 and Q2. This pushes the reagent or solvent in the CFR out to waste or to the CF, depending on which solenoid is actuated on the three way switching valve just after the CFR. The program for sequencing therefore consists of only opening and closing solenoid actuated valves at various times.

The program summary for C-terminal sequencing utilizing the sequencer depicted by FIG. 1 is set forth in Table 2.

TABLE 2

C-Terminal Sequencer Program Summary

| Continuous Flow Reactor (CFR) (45° C.) | Conversion Flask (CF) (40° C.) | Duration (sec) |
|---|---|---|
| (1) | Pressurized R1 | 3 |
| (2) | deliver R1 | 5 |
| (3) | R1 reaction | 30 |
| (4) | blow out R1 | 60 |
| (5) | R2 pressurize | 3 |
| (6) | R2 deliver | 2 |
| (7) | R2 reaction | 180 |
| (8) | Blowout R2 | 15 |
| (9) | S1 pressurize | 3 |
| (10) | S1 deliver | 10 |
| (11) | Blowout S1 | 15 |
| (12) | R4 pressurize | 3 |
| (13) | R4 deliver | 60 |

TABLE 2-continued

C-Terminal Sequencer Program Summary

| Continuous Flow Reactor (CFR) (45° C.) | Conversion Flask (CF) (40° C.) | Duration (sec) |
|---|---|---|
| (14) | Blow out R4 | 60 |
| (15) | S3 pressurize | 3 |
| (16) | S3 deliver | 30 |
| (17) | Blow out S3 | 30 |
| (18) | S2 pressurize | 3 |
| (19) | S2 deliver | 240 |
| (20) | Blow out S2 | 10 |
| (21) | S3 pressurize | 3 |
| (22) | S3 rinse | 180 |
| (23) | S3 blowout | 20 |
| (24) | S4 pressurize | 3 |
| (25) | S4 deliver | 120 |
| (26) | Blow out S4 | 30 |
| (27) | S3 pressurize | 3 |
| (28) | S3 rinse | 240 |
| (29) | S3 blowout | 20 |
| (30) | S2 pressurize | 3 |
| (31) | S2 deliver | 120 |
| (32) | pause | 5 |
| (33) | S2 to CF | 20 |
| (34) | pause | 5 |
| (35) | CF to waste | 60 |
| (36) | S2 deliver | 120 |
| (37) | Blowout S2 | 45 |
| (38) | R3 pressurize | 3 |
| (39) | R3 deliver | 2 |
| (40) | R3 reaction | 600 |
| (41) | R3 to CF | 20 |
| (42) | Dry in CF | 600 |
| (43) | R5 pressurize | 3 |
| (44) | R5 delivery to loop | 4 |
| (45) | Loop to CF | 8 |
| (46) | R5 pressurize | 3 |
| (47) | R5 delivery to loop | 4 |
| (48) | Loop to CF | 8 |
| (49) | CF vent | 3 |
| (50) | CF to HPLC | 15 |
| (51) | pause | 60 |
| (52) | pressurize S5 | 3 |
| (53) | deliver S5 | 1.5 |
| (54) | Empty CF and dry CFR | 180 |

The first four operations in the program summary involve the reagent R1. These steps are performed only once for a particular sample and are only at the beginning of a sequencing experiment. The "pressurize R1" step means that the pressure valve for R1 is opened and the R1 bottle is allowed to pressurize with argon for 30 seconds.

In the second step, deliver R1, the valve on P4 which corresponds to R1 is still open to maintain pressure on R1, but the solenoid on the reagent block (Q2) for R1 is also opened, permitting R1 to flow into the CFR. Additionally, the solenoid on the three-way switching valve (SW 1) is opened in order to permit equalization of pressure in the closed system and to allow any overflow to go to a waste bottle. This flow is maintained for five seconds. At the end of five seconds, all of the solenoid actuated valves are closed and the R1 reagent, in this case, 10% triethylamine in methanol, is allowed to react with the protein sample for 30 seconds.

To accomplish the blowout R1 step, the valve BO1 is opened to permit argon flow up into the reagent valve block (Q1 and Q2). The waste valve (SW 1) just after the CFR is also opened. This permits the argon to push the contents of the CFR out to waste. In this case, argon is pushed through the CFR for 60 seconds and then all valves are shut off.

The second group of four operations involve the reagent R2. These steps are practiced in the same was as described for R1. Thus, instead of opening and closing the valves for R1, the corresponding valves for R2, S1, R4 and S3 are used.

This sequence of four events which, as illustrated entails treatment of the protein sample with phosphoryl isothiocyanate reagent (R2), rinsing with heptane (S1), treatment with gas phase pyridine (R4), and rinsing with DMF (S3), is repeated two more times in order to push the equilibrium all the way toward thiohydantoin formation.

At this stage 90% or greater of the protein C-terminal amino acid is derivatized to a thiohydantoin. However, there is still some isothiocyanate reagent and pyridine present in the CFR or in various lines that will add UV absorbing impurities to the HPLC chromatogram of the released thiohydantoin amino acid.

The next steps (18) to (37) involve rinsing the Zitex supported peptide sample with methanol, DMF, heptane, DMF, methanol. Half way through the last methanol wash step (32), the CF is washed with the methanol in the CFR. The methanol in the CF is then sent to waste as indicated by step (35) and the residual methanol is blown out in step (37). Several other solvents could be used for this purpose.

Cleavage is accomplished in steps (38) to (42). R3 (sodium trimethylsilanolate in methanol and t-butanol) is brought into the CFR, allowed to react for 120 seconds. Then the contents of the CFR are pushed into the CF. Once in the CF the alcoholic solution containing the thiohydantoin is dried by blowing a stream of argon on it for 600 seconds. This is accomplished by opening the valves (SW 2 and SW 3) under the CF as well as the valve which vents the CF.

At this point the dried thiohydantoin amino acid in the CF must be dissolved in a solvent, e.g. 2.0% trifluoroacetic acid (R5), for injection into the HPLC. R5 is delivered twice in order to deliver the proper volume for injection (two deliveries of 55 μl). See steps (43) to (49).

Injection into the HPLC is accomplished by applying argon pressure to the CF. This is accomplished by opening the valve just above the CF (BO2) and pushing the contents of the CF into the 100 μl HPLC injection loop. The pause step S1 is 60 seconds long in order to allow the contents of the HPLC injection loop to run onto the HPLC column. The last step involves rinsing the CF with methanol and flushing both the CFR and CF with argon for 180 seconds in order to clean out the system. See steps (52)–(54). The whole cycle is then repeated as often as desired.

The injection is controlled by an optical detector described in Rusnak, U.S. Pat. No. 5,137,695.

The cycle time for the entire program takes approximately one hour.

DESCRIPTION OF THE POLYTETRAFLUOROETHYLENE SUPPORTS

The supports of this invention may be prepared from commercially available polytetrafluoroethylene film or sheet. Preferably film or sheet having a thickness from about 0.002 inches to about 0.030 inches is utilized. It is also preferred that polytetrafluoroethylene be porous. For example, a pore size of 1 to 10 microns is appropriate.

Porous polytetrafluoroethylene or "Teflon" of appropriate thickness and pore size is available from Norton Plastics Company under the tradename Zitex. See, e.g., "Norton Performance Plastics" (1987) available from the Norton Company which describes various Zitex G products and sets forth related physical properties. The Norton product identified as Zitex G-110 is preferred and has been used in the ensuing examples.

BLOTTING OF GEL PURIFIED PROTEINS ONTO POLYTETRAFLUOROETHYLENE SUPPORTS

Techniques for blotting SDS gel purified proteins onto various supports are known. See, e.g., Towbin, H., et al., *Proc. Natl. Acad. Sci.* 76:4350–4354 (1979); Matsudaira, P., *J. Biol. Chem.* 262:10035–10038 (1987); and Aebersold, R. H., et al., *J. Biol. Chem.* 261:4229–4238 (1986). Like techniques may be used to blot protein samples from SDS or similar gels onto the supports of this invention.

The SDS-PAGE (Sodium dodecyl sulfate-polyacrylamide gel electrophoresis) system used in the practice of this invention was that originally described by Laemmli, U.K. *Nature* (London) 227:680–685 (1970).

The details of this procedure are described in detail by Gardin, D. E. in *Methods in Enzymology* 182:425–441 (1990).

EXAMPLE I

Blotting of Purified Protein Onto Polytetrafluoroethylene Support

A β-lactoglobulin A sample present on a SDS-PAGE sample was blotted onto a porous polytetrafluoroethylene support (Zitex G-110) having a pore size of 1–2 microns, a pore volume of 40% and a thickness of 0.010 inches.

The Zitex was prewet by soaking in methanol and thereafter placed on top of the separating polyacrylamide gel bearing the sample. This assembly was then sandwiched between three layers of Whatman filter paper underneath the gel and three layers of Whatman filter paper on top of the Zitex. This whole assembly was then placed between two Scotch-Brite pads and placed in the electrotransfer unit. The electrotransfer buffer was 0.025M Tris, 0.192M glycine, pH 8.3. The transfer was accomplished with a constant current of 30 milliamps for three hours. Protein staining was accomplished by placing the Zitex support in a solution of 0.1% Amido Black (w/v) in 95% methanol, 5% acetic acid for 15 minutes. Destaining was accomplished by soaking the Zitex support in 95% methanol, 5% acetic acid for 5 minutes. Staining and destaining was accomplished at room temperature (22° C.).

EXAMPLE II

C-Terminal Sequencing of β-Lactoglubulin A On Zitex support

A Zitex supported β-lactoglobulin A sample (350 pmol) was subjected to C-terminal sequencing using the instrument depicted by FIG. 1, the program set forth in Table 2 and the chemistry described in co-pending Bailey and Shively U.S. patent application Ser. No. 07/801,944 in the manner described above. The results through four cycles are shown in FIG. 2.

EXAMPLE III

Automated C-Terminal Sequencing of Superoxide Dismutase on Zitex Support

A Zitex support bearing superoxide dismutase (5.2 nmol), and the instrument and the program described in Example II were utilized.

The sample was treated with acetic acid immediately prior to sequencing to acetylate the epsilon amino group of lysine and thus preclude co-elution of the thiohydantoin lysine derivative with the thiohydantoin-phe derivative. The results through four cycles are shown by the chromatograms of FIG. 3. The applicants' commonly assigned copending application Ser. No. 07/801,944 describes a process for the carboxy terminal sequencing of a peptide or polypeptide in which the carboxy terminal amino acid of the peptide is reacted with a mixture of phosphoroisothiocyanatidate and pyridine to form a thiohydantoin derivative. In lieu of pyridine, triazine, imidazole or tetrazole may be used to form the thiohydantoin derivative.

The use of the polytetrafluoroethylene supported peptide samples with the C-terminal sequencing chemistry described in co-pending application U.S. Ser. No. 07/801,944 performed in the gas phase with solvents that do not wash the sample from the polytetrafluoroethylene support makes it possible for the first time to C-terminal sequence subnmol samples of proteins through a plurality of cycles.

We claim:

1. In a process for the N-terminal or C-terminal sequencing of a supported peptide sample, the improvement which comprises sequencing a peptide sample supported on a porous polytetrafluoroethylene surface.

2. A process which comprises the carboxy terminal sequencing of a protein sample supported on a porous polytetrafluoroethylene surface.

3. A process which comprises:
   (i) directly transferring by blotting a peptide sample which has been purified by electrophoresis on an SDS gel to a porous polytetrafluoroethylene support for said sample; and
   (ii) placing said support bearing said transferred sample directly into a N-terminal or C-terminal sequencer.

4. A process as defined by claim 3 further comprising the step:
   (iii) sequencing said sample.

5. A method for the C-terminal or N-terminal sequencing of a peptide which comprises:
   (i) providing samples of said peptide on a gel,
   (ii) transferring said sample to a surface of polytetrafluoroethylene sheet, and
   (iii) subjecting said sample on said surface of said sheet to C-terminal or N-terminal sequencing.

* * * * *